US00RE39651E

(19) United States
(12) Reissued Patent
Schwartz

(10) Patent Number: US RE39,651 E
(45) Date of Reissued Patent: May 22, 2007

(54) APPARATUS FOR RAPID COOLING OF THE BRAIN AND METHOD OF PERFORMING SAME

(76) Inventor: George R. Schwartz, P.O. Box 6670, Santa Fe, NM (US) 87502

(21) Appl. No.: 09/895,623

(22) Filed: Jun. 27, 2001

Related U.S. Patent Documents

Reissue of:
(64) Patent No.: 5,916,242
Issued: Jun. 29, 1999
Appl. No.: 08/816,255
Filed: Mar. 13, 1997

U.S. Applications:
(60) Provisional application No. 60/030,030, filed on Nov. 4, 1996.

(51) Int. Cl.
*A61F 7/12* (2006.01)

(52) U.S. Cl. ..... 607/113
(58) Field of Classification Search ..... 600/120; 604/43; 607/96, 104, 105, 107, 113; 606/20, 606/21, 22, 23, 24, 25, 26
See application file for complete search history.

(56) References Cited

U.S. PATENT DOCUMENTS

| | | | | |
|---|---|---|---|---|
| 3,976,065 A | | 8/1976 | Durkan | 128/145.8 |
| 4,423,725 A | | 1/1984 | Baran et al. | 128/207.15 |
| 4,552,149 A | | 11/1985 | Tatsuki | 128/402 |
| 5,261,399 A | | 11/1993 | Klatz et al. | 607/104 |
| 5,314,456 A | | 5/1994 | Cohen | 607/109 |
| 5,480,417 A | * | 1/1996 | Hascoet et al. | 607/101 |
| 6,149,624 A | * | 11/2000 | McShane | 604/113 |
| 6,321,121 B1 | * | 11/2001 | Zelickson et al. | 607/101 |
| 6,325,818 B1 | * | 12/2001 | Werneth | 604/103.06 |

FOREIGN PATENT DOCUMENTS

| | | | | |
|---|---|---|---|---|
| WO | WO 91/05528 | * | 5/1991 | 607/113 |

OTHER PUBLICATIONS

Critical Care Medicine, 1996, vol. 24, No. 6, pp. 911–914.*

* cited by examiner

*Primary Examiner*—Lee S. Cohen
(74) *Attorney, Agent, or Firm*—Stephen A. Slusher; Peacock Myers, P.C.

(57) ABSTRACT

Rather than cooling the brain by the relatively slow heat conduction through the low heat conductivity of the bony skull and hair covering the head, the present invention teaches the use of a light weight, easily applied neck encircling collar in firm contact with the soft tissue of the neck, and particularly in good thermal contact with the carotid arteries traversing the neck. A coolant flowing through channels embedded in the collar rapidly cools the blood flowing through the carotid arteries which branch into blood vessels throughout the brain providing vascular access and attendant rapid internal cooling throughout the brain including its deepest recesses. Placing the collar on the patient's neck is easily and quickly accomplished simultaneously with other emergency medical techniques, such as CPR, which maintain the patient's heart and lung activity. The collar of the invention contains no metallic parts; the collar, including the coolant channel, may be non-metallized fabric or plastic. This allows X-ray, Cat scan, or MRI procedures to be used while the collar is in place without impairing the effectiveness of the procedure. In a second embodiment, a conventional endotracheal tube, inserted into the trachea is provided with an toroidal bladder surrounding the tube. The toroidal bladder is positioned at the back of the oral cavity, and a coolant flowing through the toroid cools blood vessels in the oral cavity which traverse the brain, providing cooling of the brain tissue.

5 Claims, 3 Drawing Sheets

APPARATUS FOR RAPID COOLING OF THE BRAIN AND METHOD OF PERFORMING SAME

Matter enclosed in heavy brackets [ ] appears in the original patent but forms no part of this reissue specification; matter printed in italics indicates the additions made by reissue.

This application claims the benefit of U.S. Provisional Application No. 60/030,030 filed Nov. 4, 1996.

BACKGROUND OF THE INVENTION

1. Field of the Invention

This invention relates to apparatus and method for cooling the brain, and in particular to apparatus and method for inducing hypothermia throughout the tissues of the brain.

2. Description Relative to the Prior Art

It is well known in the medical art that depriving the brain of oxygen for even a short period of time results in irreversible damage to the brain tissue. Such deprivation occurs during stroke, respiratory arrest, cardiac arrest, trauma and other severe bodily disturbances that slow or otherwise hinder the flow of oxygenated blood to the brain. However, it is also known that lowering the temperature of the brain (hypothermia) slows its metabolic activity, and reduces the chance of tissue damage when the oxygen supply is diminished.

At present, operative neurosurgery and cardiac surgery is done in many cases using hypothermia for the specific purposes of maintaining cerebral and cardiac function. In an operating room, this requires use of a cooling module in conjunction with heart/lung bypass techniques by which the patient's blood, and resultantly the patient's brain tissue, is cooled. This widespread ability to rapidly lower brain temperature by as little as four or five degrees can make an enormous difference in preservation of function. However, out in the field, when medical emergencies occur, brain cooling must quickly and expeditiously take place without access to the sophisticated equipment available in the hospital operating room. A portable brain cooling apparatus usable in the field is described in U.S. Pat. No. 5,261,399, issued in the names of Klatz et al. For use on an injured or disabled patient, the patent discloses a helmet and back plate containing cavities in which a coolant flows to cool the brain by means of heat conduction through the skull and upper spinal column.

SUMMARY OF THE INVENTION

Rather than cooling the brain by the relatively slow heat conduction through the low heat conductivity of the bony skull and hair covering the head, the present invention teaches the use of a light weight, easily applied neck encircling collar in firm contact with the soft tissue of the neck, and particularly in good thermal contact with the carotid arteries traversing the neck. A coolant flowing through channels embedded in the collar rapidly cools the blood flowing through the carotid arteries which branch into blood vessels throughout the brain providing vascular access and attendant rapid internal cooling throughout the brain including its deepest recesses. Placing the collar on the patient's neck is easily and quickly accomplished simultaneously with other emergency medical techniques, such as CPR, which maintain the patient's heart and lung activity.

The collar of the invention contains no metallic parts; the collar, including the coolant channel, may be non-metallized fabric or plastic. This allows X-ray, Cat scan, or MRI procedures to be used while the collar is in place without impairing the effectiveness of the procedure.

In a second embodiment for rapid internal cooling of the brain, a conventional endotracheal tube, inserted into the trachea, is provided with an toroidal bladder surrounding the tube. The toroidal bladder is positioned at the back of the oral cavity, and a coolant flowing through the toroid cools blood vessels in the oral cavity which also traverse the brain, providing cooling of the brain tissue.

*The endotracheal tube and the bladder are made from materials including non-metallic fabric or plastic materials, such that these components are compatible with X-ray, MRI or CAT scan procedures.*

The coolant flowing through the channels of the collar or the toroidal bladder may be any of the well known liquid or gaseous refrigerants, for example, gaseous $CO_2$, freon, or ice water, pumped through the channels of the collar or toroidal bladder in a manner known in the refrigeration art.

BRIEF DESCRIPTION OF THE DRAWINGS

The invention will be described with respect to the drawings, of which.

DESCRIPTION OF THE PREFERRED EMBODIMENTS OF THE INVENTION

Figure 1:
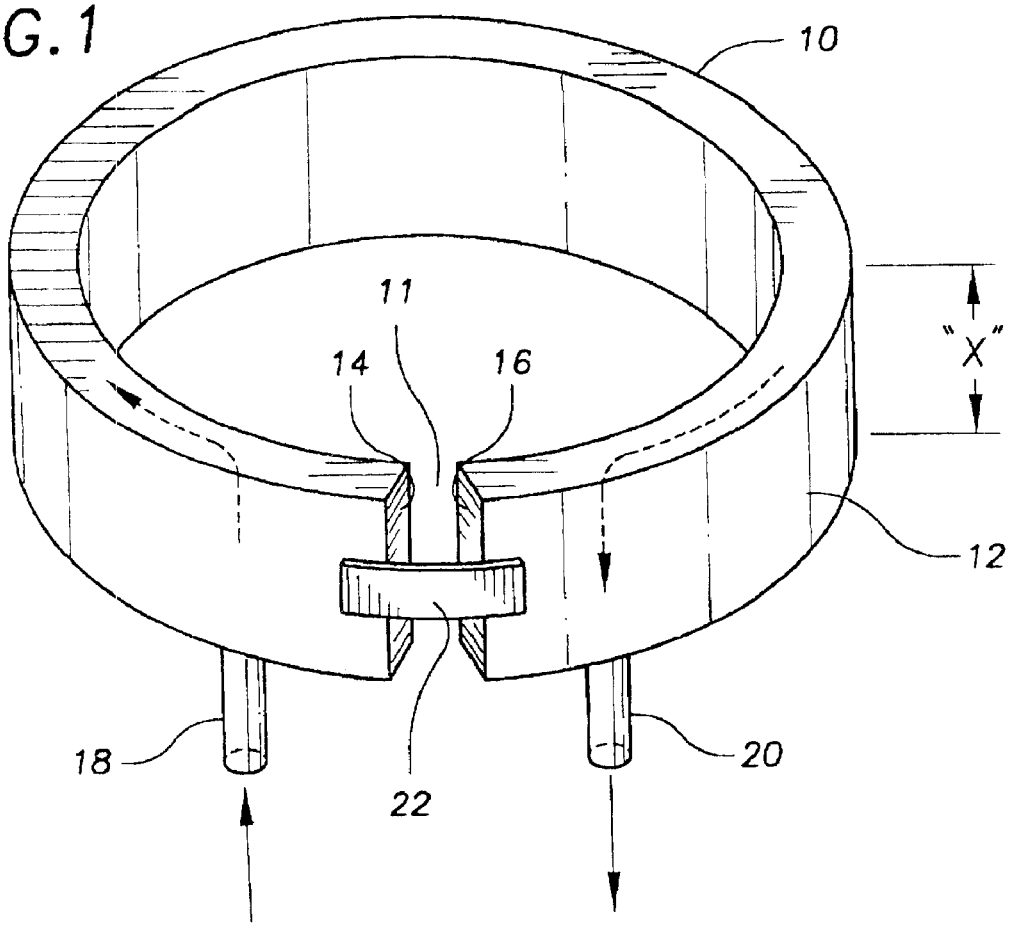
FIG. 1 is a drawing of the collar of the invention.

Referring to FIG. 1, a substantially circular collar 10, containing a gap 11, has a channel 12 running about the circumference of the collar 10. The ends 14,16 of the channel 10 are sealed, leaving the gap 11 in the collar 10. Inlet tube 18 and outlet tube 20, located proximate to the ends 14,16, serve as entrance and exit for a coolant flowing through the collar 10 in channel 12. The collar's height "X" is sufficient to cover a large portion of the carotid artery in the neck of a patient having the collar 10 in place. A fastener 22, such as a Velcro strip, is used to firmly secure the collar 10 about the neck of the patient. The collar 10 is fabricated from either a fabric or plastic having a good thermal transfer coefficient, and capable of sustaining coolant fluid flow through the channel 12 without leakage.

Figure 2:
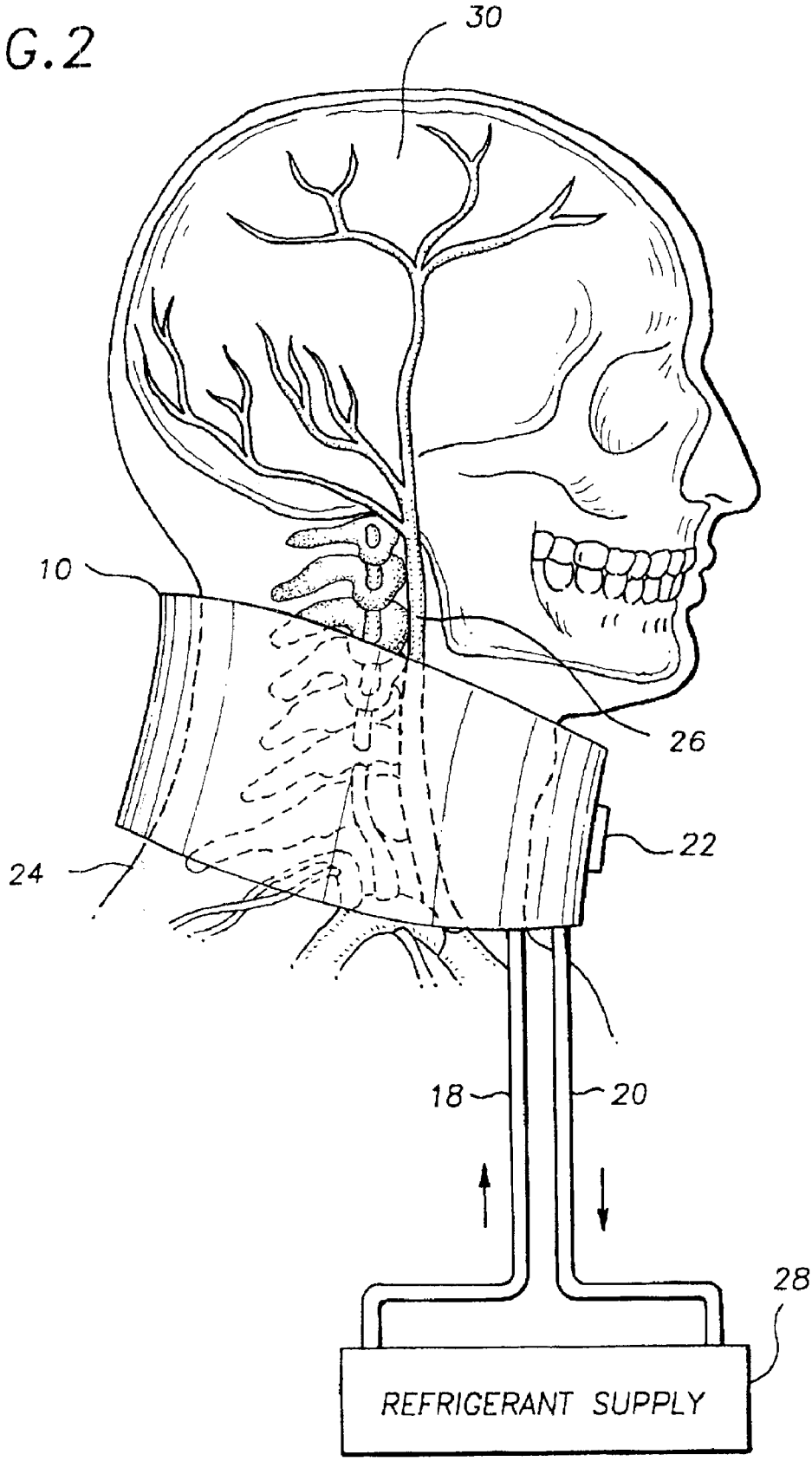
FIG. 2 is a drawing of the collar of FIG. 1 in place around a patient's neck.

Referring to FIG. 2, the collar 10 is shown in position on the neck 24 of a patient. The collar 10 is in contact with the carotid artery 26 substantially over the full distance where the carotid artery 26 traverses the neck 24. The collar 10 is firmly secured in position against the skin of the neck 24, and is in solid contact over the carotid artery 26. Coolant flows from the refrigerant supply 28 via the inlet tube 18 through the channel 12 of the collar 10 and back down to the refrigerant supply 28 via the outlet tube 20, cooling the carotid artery 26 as well as other vascular vessels in the neck 24, and attendantly the brain 30.

Figure 4:
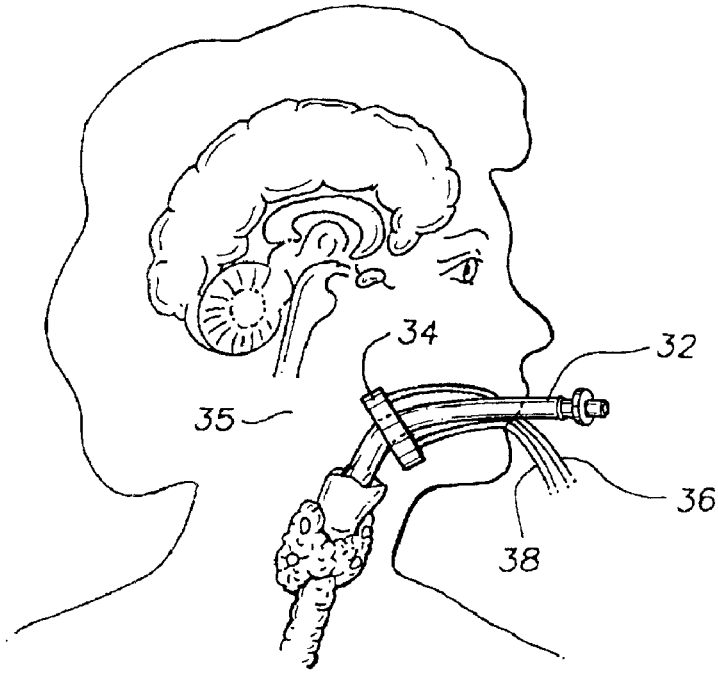
FIG. 4 is a drawing of the second embodiment of the invention in use with a patient.
Figure 3:
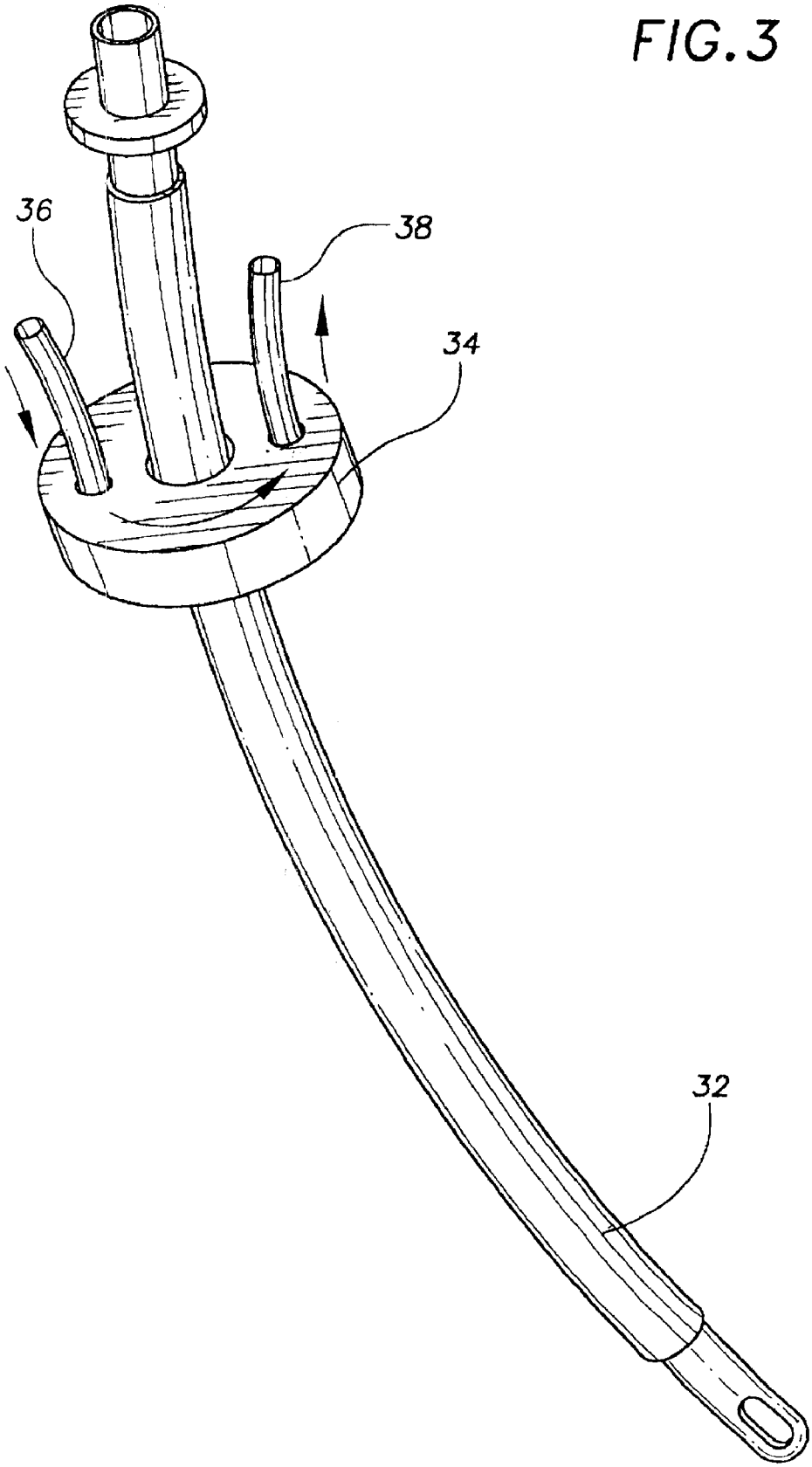
FIG. 3 is a drawing of a second embodiment of the invention.

In FIG. 3, an endotracheal tube 32 known in the art, has a toroidal shaped bladder 34 positioned to surround the endotracheal tube 32 proximate the end which is inserted into a patient's trachea. When the tube 32 is in use, (FIG. 4), the bladder 34 is in intimate contact with the back of the patient's oral cavity 35. The bladder 34 has inlet and outlet tubes 36,38 which carry coolant that flows through the bladder 34, cooling the back of the oral cavity 35, and attendantly the blood vessels located in the oral cavity 35. These blood vessels are both adjacent to the brain and connect to the brain, and hence cooling these blood vessels also provides cooling of the brain tissue. The bladder 34 may either be rubber or a flexible plastic which will conform to the shape of the oral cavity 35, and will make firm contact with the tissues and vessels of the oral cavity 35. This second embodiment of the invention may be used in conjunction with the first embodiment described above, in which case the same refrigerant supply 28 is connected to both the inlet tubes 18, 36 and outlet tubes 20, 38. Or, when used alone, a refrigerant supply equivalent to the refrigerant supply 28 of FIG. 2 is connected to the tubes 36,38.

The invention has been described in detail with particular reference to preferred embodiments thereof, but it will be understood that variations and modifications can be effected within the spirit and scope of the invention. For example, the first embodiment of the invention may be incorporated into a neck support collar used for supporting an injured patient's head.

What is claimed is:

1. Apparatus for inducing hypothermia in a patient's brain, said apparatus comprising:

a) an endotracheal tube having a first end and second end, b) a toroidal shaped bladder surrounding said tube proximate said first end of said tube, said first end for insertion into [said] *a* patient's trachea whereby said bladder contacts the tissues and blood vessels of [said] *a* patient's oral cavity, c) a source of liquid or gaseous coolant, said source for providing coolant to said bladder, d) inlet and outlet coolant conducting elements connected to said toroidal shaped bladder, whereby said coolant from said source flowing through said inlet and outlet coolant conducting elements cools said bladder, further whereby when said first end of said endotracheal tube is inserted into [said] *a* patient's trachea, said coolant flowing in said bladder lowers the temperature of [said] *the* tissues and blood vessels of [said] *a* patient's oral cavity in contact with said bladder, [said] *the* tissues and blood vessels further acting as heat conducting paths from [said] *a patient's* brain to said bladder whereby the temperature of [said] *the* brain is lowered.

2. The apparatus of claim 1 wherein said endotracheal tube and said bladder comprises non-metallic fabric or plastic materials, whereby said apparatus is compatible with X-ray, MRI or CAT scan procedures.

3. The apparatus of claim 1 further comprising refrigeration means supplying said coolant.

[4. A method of inducing hypothermia in a patient's brain comprising the step of:

a) cooling said brain by lowering the temperature of the blood flowing in blood vessels located in said patient's oral cavity, b) inserting an endotracheal tube into contact with said patient's trachea, said endotracheal tube having a toroidal bladder surrounding said endotracheal tube, said bladder being in contact with blood vessels located at the rear of said patient's oral cavity, c) flowing coolant through said bladder by means of an inlet tube to said bladder and an outlet tube from said bladder, whereby said blood vessels are lowered in temperature to cool said brain.]

[5. The method of claim 4 further comprising the steps of:

a) inserting an endotracheal tube into contact with said patient's trachea, said endotracheal tube having a toroidal bladder surrounding said endotracheal tube, said bladder being in contact with blood vessels located at the rear of said patient's oral cavity and b) flowing coolant through said bladder by means of an inlet tube to said bladder and an outlet tube from said bladder, whereby said blood vessels are lowered in temperature to cool said brain.]

*6. A method of inducing hypothermia in a patient's brain, comprising the steps of:*

*a) inserting a coolant contact comprising a bladder, an inlet coolant conducting tube and an outlet coolant conducting tube into the oral cavity of the patient, the bladder being in contact with tissues proximate blood vessels located at the rear of the patient's oral cavity; and*

*b) flowing coolant through the bladder by means of the inlet coolant conducting tube and the outlet coolant conducting tube, whereby the tissues and blood vessels are lowered in temperature to cool the brain.*

*7. The method of claim 6 wherein the bladder is a toroidal bladder and the coolant contact further comprises an endotracheal tube, wherein the toroidal bladder surrounds the endotracheal tube.*

* * * * *